(12) United States Patent
Lim et al.

(10) Patent No.: US 10,701,498 B2
(45) Date of Patent: Jun. 30, 2020

(54) SYSTEMS AND METHODS FOR TREATING TINNITUS AND ENHANCING HEARING

(71) Applicant: REGENTS OF THE UNIVERSITY OF MINNESOTA, Minneapolis, MN (US)

(72) Inventors: Hubert H. Lim, Minneapolis, MN (US); Cory D. Gloeckner, Minneapolis, MN (US); Yezihalem Mesfin, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/616,278

(22) Filed: Jun. 7, 2017

(65) Prior Publication Data

US 2017/0353807 A1 Dec. 7, 2017

Related U.S. Application Data

(60) Provisional application No. 62/346,798, filed on Jun. 7, 2016.

(51) Int. Cl.
| | |
|---|---|
| *H04R 25/00* | (2006.01) |
| *A61B 5/12* | (2006.01) |
| *G10K 11/175* | (2006.01) |
| *A61N 1/36* | (2006.01) |
| *A61N 1/04* | (2006.01) |

(52) U.S. Cl.
CPC ............. *H04R 25/75* (2013.01); *A61B 5/128* (2013.01); *A61N 1/0456* (2013.01); *A61N 1/0476* (2013.01); *A61N 1/36034* (2017.08); *A61N 1/36036* (2017.08); *G10K 11/175* (2013.01); *G10K 2210/1081* (2013.01); *G10K 2210/116* (2013.01); *H04R 25/554* (2013.01); *H04R 2225/021* (2013.01)

(58) Field of Classification Search
CPC .............................. H04R 25/75; H04R 25/554; H04R 2225/021; A61N 1/36034; A61N 1/36036; A61N 1/0456; A61N 1/0476; A61B 5/128; G10K 11/175; G10K 2210/1081; G10K 2210/116
USPC .......................................................... 607/55
See application file for complete search history.

(56) References Cited

U.S. PATENT DOCUMENTS

| | | | |
|---|---|---|---|
| 4,982,434 A | 1/1991 | Lenhardt et al. | |
| 5,721,783 A * | 2/1998 | Anderson | H04B 1/385 381/312 |
| 6,217,508 B1 | 4/2001 | Ball et al. | |
| 8,929,575 B2 | 1/2015 | Norris | |
| 2011/0004274 A1 * | 1/2011 | Schleich | A61N 1/36036 607/57 |
| 2012/0053391 A1 | 3/2012 | Mishelevich | |

(Continued)

FOREIGN PATENT DOCUMENTS

KR 100799197 B1 * 1/2008 .............. A61F 11/00

*Primary Examiner* — Erin M Piateski
(74) *Attorney, Agent, or Firm* — Quarles & Brady LLP

(57) ABSTRACT

Systems and methods for treating hearing loss and/or tinnitus or enhancing hearing to sounds or sound features such as in a noisy environment are disclosed. An apparatus includes a hearing aid and associated electrodes for electrically stimulating a portion near, on or in the ear, where the electrical stimulation is synchronized with a sound input and/or sound output of the hearing aid.

12 Claims, 9 Drawing Sheets

(56) References Cited

U.S. PATENT DOCUMENTS

| | | | |
|---|---|---|---|
| 2012/0109006 A1* | 5/2012 | James | A61N 1/37247 |
| | | | 600/559 |
| 2014/0126752 A1 | 5/2014 | Beck et al. | |
| 2014/0275737 A1* | 9/2014 | Shore | A61M 21/02 |
| | | | 600/26 |
| 2016/0151629 A1* | 6/2016 | Chalupper | A61N 1/36036 |
| | | | 607/57 |

* cited by examiner

SYSTEMS AND METHODS FOR TREATING TINNITUS AND ENHANCING HEARING

CROSS REFERENCE TO RELATED APPLICATIONS

This application is based on, claims priority to, and incorporates herein by reference in its entirety U.S. Provisional Application Ser. No. 62/346,798, filed Jun. 7, 2016, and entitled, "Apparatus for Treating Tinnitus and Hearing Enhancement and Related Methods." The references cited in the above provisional patent application are also hereby incorporated by reference.

FIELD OF THE INVENTION

This document concerns an invention relating generally to treating tinnitus and enhancing hearing by electrically stimulating near or in the auditory system in combination with acoustic stimulation.

BACKGROUND

Tinnitus is a phantom sound percept that exists without any external sound source. Although it is known as ringing in the ear, it is actually a neurological disorder in which abnormal signaling patterns occur in brain regions responsible for auditory perception. Tinnitus continues to be underestimated in terms of its negative impact in society because it is not a condition that is visible to the public. About 250 million people worldwide experience chronic tinnitus that can be bothersome on a daily basis. In the U.S. alone, approximately 16 million people have sought medical attention for tinnitus, with 2-3 million experiencing debilitating and even suicidal conditions (e.g., related to annoyance, depression, anxiety, headaches, insomnia). Considering the link between tinnitus and hearing loss, these numbers will continue to rise due to increased noise in our environment, a larger elderly population, and greater noise-based war injuries. In fact, tinnitus is currently the highest service-connected disability for veterans and the top war-related health cost. Unfortunately, there is no cure or reliable treatment for tinnitus. Various drug therapies, neural and mechanical stimulation methods, psychotherapy, and sound treatments have been attempted but with mixed results.

There is a general consensus in the tinnitus field that most of the tinnitus cases are linked to some form of hearing loss that alters the firing patterns in the auditory system and leads to tinnitus, and thus approaches for restoring hearing loss including hearing aids and cochlear implants can serve as potential solutions. It is not possible to provide a cochlear implant to most of these patients because this device can compromise their residual hearing since the implant is inserted into the cochlea. Hearing aids can amplify sounds to attempt to restore hearing but in most tinnitus patients, this hearing restoration is insufficient to treat the tinnitus. Due to these limitations, a majority of researchers attempt to find ways to modulate the brain with devices, drugs, or psychotherapy/counseling to shift the abnormal brain patterns back to normal or at least to a stable state without the tinnitus percept. Currently, there is no consistent or reliable method for treating tinnitus. Some approaches work in some tinnitus patients, but there is no way yet to predict beforehand who will respond to a given treatment. As a result, clinicians or audiologists can only provide a list of "potential" solutions to the patients, which typically includes counseling to deal with the tinnitus or a tinnitus masker. Tinnitus maskers are devices that present different types of sounds to attempt to interfere with or suppress the tinnitus percept though they typically do not sufficiently alter the brain activity to be effective in most patients. If the tinnitus is more bothersome to the patient, he or she can be prescribed anti-depressants or anti-anxiety medications to help cope with the tinnitus but these do not necessarily treat the tinnitus percept.

Since research in the tinnitus field has demonstrated abnormal brain patterns in tinnitus patients and animals, it has become increasingly accepted by scientists and clinicians that one way to treat tinnitus is to shift the abnormal neural activity to a near-normal or non-tinnitus state. There are various investigational approaches to alter this abnormal tinnitus activity, known as neuromodulation devices. Electrodes can be implanted into the brain or nerves for direct electrical stimulation. Noninvasive approaches using magnetic (TMS) and electrical (tDCS, tACS, TENS) fields or even mechanical inputs (e.g., acupuncture, body movements/exercise) can also be attempted. Invasive approaches require risky surgery and are expensive, limiting the number of patients who can benefit from those treatments. The noninvasive approaches have not shown sufficient brain changes to treat tinnitus consistently across patients. Accordingly, more improved methods to treat tinnitus are needed.

In terms of hearing loss, more than 5% of the population (more than 360 million people) have disabling hearing loss (according to the World Health Organization). The most common solution is to wear a hearing aid. Hearing aids are designed to amplify sound features that the patient cannot hear sufficiently. In some cases, this approach works well but in many patients, especially in noisy and complex environments, this approach is insufficient. Simply amplifying these different sound features, especially different frequency components (i.e., many have hearing deficits for specific or a range of sound frequencies), causes them to distort or mask other sound features. Furthermore, amplifying sounds causes feedback issues for hearing aids since the sound that is amplified can be picked up again by the microphone, which in turn gets re-amplified and so on.

What would be a major breakthrough in the hearing aid field is if we could increase the gain of those desired sound features in the brain (and suppress the unwanted sound features) rather than physically at the output of the hearing aid to the ear. There are damaged portions of the middle and inner ear that lead to deficits in hearing of specific sound features. Unless those damaged portions are fixed, then the only way to overcome those deficits is to amplify those sound features to get them through those damaged portions. Amplifying those sound features can create significant distortion of the original sound input and even become uncomfortable or unintelligible for the patient. Accordingly, more improved methods to treat hearing loss are needed.

SUMMARY OF THE PRESENT DISCLOSURE

In one or more embodiments, an apparatus includes a hearing aid device for hearing rehabilitation that is combined and/or paired with electrical stimulation using coordinated, for example, precisely timed patterns relative to the sound input. The hearing aid device includes a sound input and a sound output. The apparatus further includes one or more electrodes communicatively coupled with the hearing aid device. The electrodes are configured to provide electrical stimulation to one or more of an area on a head near an ear or on or within the ear, where the electrical stimulation is synchronized with the sound output.

In one or more embodiments, an apparatus includes a hearing aid device to suppress tinnitus/hyperacusis, where the sound input receives a signal and a processor processes the signal through a band pass filter to separate the signals into different bands based on a particular feature or features, such as electrical pulses with a set delay relative to a broadband noise or complex stimulus that is repeated multiple times to suppress the phantom percept.

In one or more embodiments, an apparatus is used for hearing rehabilitation, in which the electrical pulses are synchronized with portions of the sound input that are low energy and difficult to hear. This can be done during training sessions where certain types of sound stimuli and features that are usually difficult to hear for a given patient (e.g., high frequency sounds) are paired with ear electrical stimulation to enhance coding to those inputs. This apparatus can also be applied to normal hearing people who want to improve their hearing or sensitivity to certain sound features such as speech in noisy environments or specific words of a new language.

In one or more embodiments, an apparatus for treating tinnitus and/or hearing loss includes a hearing aid device having a sound input and a sound output, and one or more electrodes communicatively coupled with the hearing aid device, where the electrodes are configured to provide electrical stimulation to one or more of an area on a head near an ear or on or within the ear, and the electrical stimulation is synchronized with a sound sent to the sound output.

In one or more embodiments, the electrical stimulation is synchronized with delivery of a modified signal or the features of the modified or original signal to the sound output.

In one or more embodiments, the one or more electrodes are coupled with a pinna region of the ear.

In one or more embodiments, the one or more electrodes are coupled with a mastoid region of the ear.

In one or more embodiments, the one or more electrodes are coupled with an inner ear channel.

In one or more embodiments, the one or more electrodes are coupled directly with the hearing aid device.

In one or more embodiments, the apparatus further includes an inner ear insert having an inner ear electrode, the inner ear insert coupled with the hearing aid device.

In one or more embodiments, the hearing device further includes a processor, the processor configured to collect a signal, filter or process the signal, detect a feature or features from the signal, reconstruct the signal, and deliver the reconstructed signal to the sound output.

In one or more embodiments, the processor is configured to deliver specific sound stimuli through the sound output while delivering electrical pulses with the one or more electrodes to suppress a phantom percept.

In one or more embodiments, an apparatus for treating tinnitus, reducing pain, suppressing undesirable sounds, and/or enhancing hearing includes a hearing aid device having one or more electrodes, where the hearing aid device includes a sound input and a sound output. The hearing aid device further includes a processor configured to: collect a signal, filter or process the signal, detect a feature or features from the signal, reconstruct the signal, and deliver the reconstructed signal to the sound output. The apparatus further includes an electrical stimulator coupled with the processor, where the electrical stimulator electrically coupled with the one or more electrodes, and the electrodes are configured to provide electrical stimulation to one or more of an area on a head near an ear or on or within the ear, and the electrical stimulation is synchronized with features of the modified or original signal sent to the sound output.

In one or more embodiments, the electrical stimulation is also synchronized with delivery of a modified signal to the sound output.

In one or more embodiments, the one or more electrodes are coupled with a pinna region of the ear.

In one or more embodiments, the one or more electrodes are coupled with a mastoid region of the ear.

In one or more embodiments, the electrodes are coupled with an inner ear channel.

In one or more embodiments, the electrodes are coupled directly with the hearing aid device.

In one or more embodiments, the apparatus further includes an inner ear insert having an electrode, the inner ear insert coupled with the hearing aid device.

In one or more embodiments, the processor is configured to deliver specific sound stimuli through the sound output while delivering electrical pulses with the electrodes to suppress a phantom percept.

In one or more embodiments, an apparatus for treating tinnitus and/or hearing loss includes a hearing aid device having an array of electrodes and a sound input and a sound output. The hearing aid device further includes a processor configured to collect a signal, filter or process the signal, detect a feature or features from the signal, reconstruct the signal, and deliver the reconstructed signal to the sound output. The array of electrodes are configured to provide electrical stimulation to one or more of an area on a head near an ear or on or within the ear, where the electrical stimulation is synchronized with the signal delivery.

In one or more embodiments, the electrical stimulation is synchronized with delivery of a modified signal to the sound output.

In one or more embodiments, at least one of the electrodes is coupled with a pinna region of the ear.

In one or more embodiments, the electrodes are coupled with a mastoid region of the ear. In one or more embodiments, the electrodes are coupled with an inner ear channel.

In one or more embodiments, the electrodes are coupled directly with the hearing aid device.

In one or more embodiments, the apparatus further includes an inner ear insert having an electrode, the inner ear insert coupled with the hearing aid device.

In one or more embodiments, the processor is configured to deliver specific sound stimuli through the sound output while delivering electrical pulses with the electrodes to suppress a phantom percept.

In one or more embodiments, a method for treating one or more of tinnitus or hearing loss includes collecting incoming sound using a sound input of an apparatus, the apparatus includes a hearing aid device having the sound input and a sound output, and one or more electrodes communicatively coupled with the hearing aid device, the electrodes configured to provide electrical stimulation to one or more of an area on a head near an ear or on or within the ear. The method further includes transducing sound to a signal, passing the signal through one or more band pass filters, detecting a feature or features of the signal over time, modifying the signal based on feature detection, delivering the signal through the sound output, delivering electrical stimulus using the electrodes, where delivery of the electrical stimulus is synchronized with delivery of the signal.

In one or more embodiments, the method further includes amplifying the signal prior to delivering the signal through the sound output.

In one or more embodiments, the method further includes determining a delay to enhance deficits in the incoming sound, and delaying delivery of the signal corresponding to the determined delay.

In one or more embodiments, delivering electrical stimulus includes delivering electrical stimulus to a mastoid region.

In one or more embodiments, delivering electrical stimulus includes delivering electrical stimulus to a pinna.

In one or more embodiments, delivering electrical stimulus includes delivering electrical stimulus to an inner ear region.

In one or more embodiments, the method further includes delivering specific sound stimuli through the sound output while delivering electrical pulses with the electrodes to suppress a phantom percept.

In one or more embodiments, presenting specific sound stimuli includes presenting one or more of pure tones, customized chords, or bandwidth noise.

In one or more embodiments, the method further includes pairing and presenting the specific sound stimuli with electrical biphasic pulses in timed patterns.

In one or more embodiments, an apparatus for treating tinnitus, reducing pain, suppressing undesirable sounds, and/or enhancing hearing includes a hearing aid device with a sound input and a sound output, and one or more electrodes communicatively coupled with the hearing aid device, the electrodes configured to provide electrical stimulation to one or more of an area on a head near an ear or within or on the ear via electrical impulses.

In one or more embodiments, the apparatus further includes a processor configured to receive a sound signal using the sound input, filter or process the sound signal, detect features in the sound signal, reconstruct the sound signal to generate a modified signal and identify the times (e.g., start and/or stop times) of the features in the modified or original signal, and deliver the modified or original sound signal to the sound output.

In one or more embodiments, the processor is further configured to use the electrodes to deliver electrical impulses that are synchronized with the sound signal to the sound output with delays between the electrical pulses and sound features detected in the sound signal to the sound output, wherein delays are between 0 and 100 milliseconds.

In one or more embodiments, electrical stimulation is synchronized with delivery of the modified or original signal to the sound output or different features of the modified or original signal to the sound output, wherein the modified signal or features includes one or more signals selected from the group consisting of a bandpass filtered signal, a frequency-specific gain adjusted signal, a temporally-stretched or spectrally-stretched signal, a temporally-compressed or spectrally-compressed signal, a custom filtered signal, an envelope or temporal fine structure extracted signal, a signal extracted using independent component analysis, a signal extracted using noise suppression or cancellation algorithms; and/or a signal extracted using Hilbert Transform.

In one or more embodiments, detected features include one or more of peaks or troughs of the sound signal or of the modified signal, steepest slopes of the sound signal or modified signal, low probability patterns in the sound signal or modified signal, low energy patterns in the sound signal or modified signal, rapidly changing patterns in the sound signal or modified signal; and/or onsets and/or offsets of critical segments of the sound signal or modified signal, wherein the critical segments can include a start or end of a word or phoneme in the sound signal or modified signal.

In one or more embodiments, the apparatus further includes an inner ear insert with one or more inner ear electrodes. The inner ear insert may be coupled with the hearing aid device.

In one or more embodiments, the processor is configured to deliver specific sound stimuli through the sound output while delivering electrical pulses with the one or more electrodes to synchronize to different sound features with delays of 0 ms to 100 ms to enhance or suppress sensitivity to those sound features.

In one or more embodiments, an apparatus for treating tinnitus, reducing pain, suppressing undesirable sounds, and/or enhancing hearing includes a sound input and a sound output, one or more electrodes for electrically stimulating a portion near, on or in the ear, an electrical stimulator electrically coupled with the one or more electrodes and configured to supply the one or more electrodes with electrical pulses, and a processor coupled with the sound input, the sound output, and the electrical stimulator, with the processor configured to receive a sound signal via the sound input, filter or process the sound signal, detect features in the sound signal, reconstruct the sound signal to generate a modified signal and identify the times of the features in the modified or original signal, and deliver the modified or original sound signal to the sound output, and use the electrical stimulator to provide, via the one or more electrodes, electrical pulses that are synchronized with the sound features detected in the sound signal being delivered using the sound output.

In one or more embodiments, a method for treating one or more of tinnitus or hearing loss includes collecting incoming sound (such as from a microphone, recorded device, cell phone or a sound generator) and transducing the incoming sound to a sound signal, passing the sound signal through one or more band pass filters, detecting a feature or features of the sound signal over time, modifying the sound signal based on feature detection, delivering the modified sound signal through a sound output, and using electrodes to deliver an electrical stimulus to one or more of an area on a head near or on an ear or within the ear via electrical pulses, where delivery of the electrical stimulus is synchronized with delivery of the modified sound signal through the sound output with a delay between 0 ms and 100 ms with the detected feature or features to enhance or suppress brain sensitivity to the feature or features.

In one or more embodiments, the sound signal is amplified prior to delivering the signal through the sound output.

In one or more embodiments, the delay is determined so as to enhance deficits in the incoming sound, and delivery of the sound signal delayed according to the determined delay.

In one or more embodiments, specific sound stimuli are delivered through the sound output while electrical pulses are delivered with the electrodes to suppress unwanted sounds or to enhance hearing to desired sounds.

In one or more embodiments, presenting sound stimuli includes presenting specific words, phonemes, features of words, music, or features of music.

In one or more embodiments, presenting sound stimuli includes presenting speech or speech features in noise to enhance sensitivity to the speech or speech features, and reduce sensitivity to the noise or unwanted sounds.

In one or more embodiments, the electrical pulses have a constant pulse rate of repeated pulses, or are varying inter-pulse timed pulses based on when sound features are detected, to enhance or suppress sensitivity to certain sound features that occur over time via single electrical pulses or bursts of electrical pulses.

In one or more embodiments, the electrical pulses or bursts of pulses are constant amplitude or amplitude modulated over time, wherein the bursts of pulses have pulse trains with a range of 100 to 5000 pulses per second (pps).

In one or more embodiments, delivery of the electrical stimulus is synchronized with detected features of the signal with each pulse or burst of pulses delayed from the sound features by 0 ms to 100 ms.

These example approaches can be applied to hearing loss, as well as to improving hearing of desired sound features for people with normal (i.e., uncompromised or minimally compromised) hearing, so as to, for example, improve hearing in noisy environments or increase sensitivity to specific sound features of languages or music. These and other embodiments, aspects, advantages, and features of the present invention will be set forth in part in the description which follows, and will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents. The accompanying drawings illustrate one or more implementations, and these implementations do not necessarily represent the full scope of the invention.

DETAILED DESCRIPTION OF THE PRESENT DISCLOSURE

Figure 1:
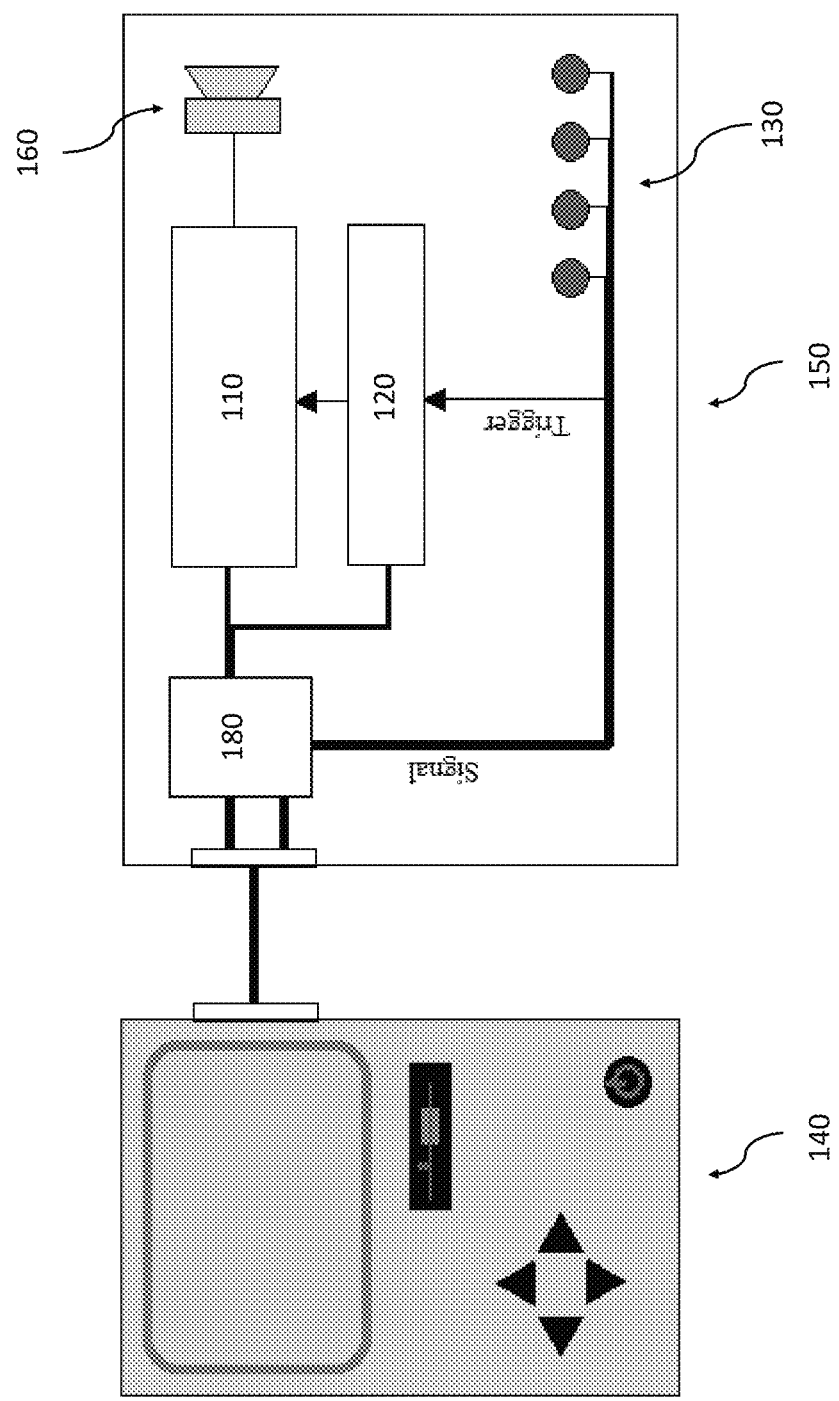
FIG. 1 illustrates a block diagram of an example apparatus in accordance with one or more embodiments.
Figure 2:
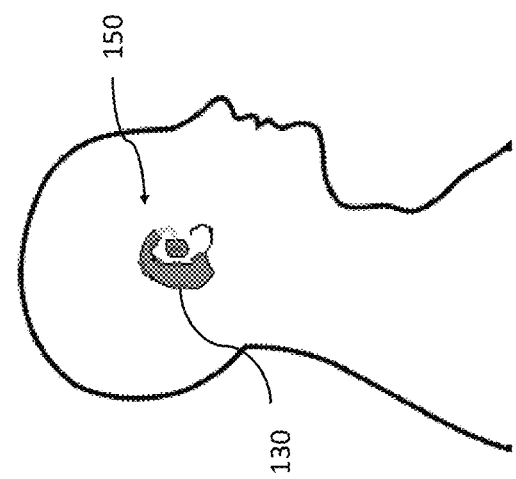
FIG. 2 illustrates a block diagram of an example apparatus in accordance with one or more embodiments.
Figure 3:
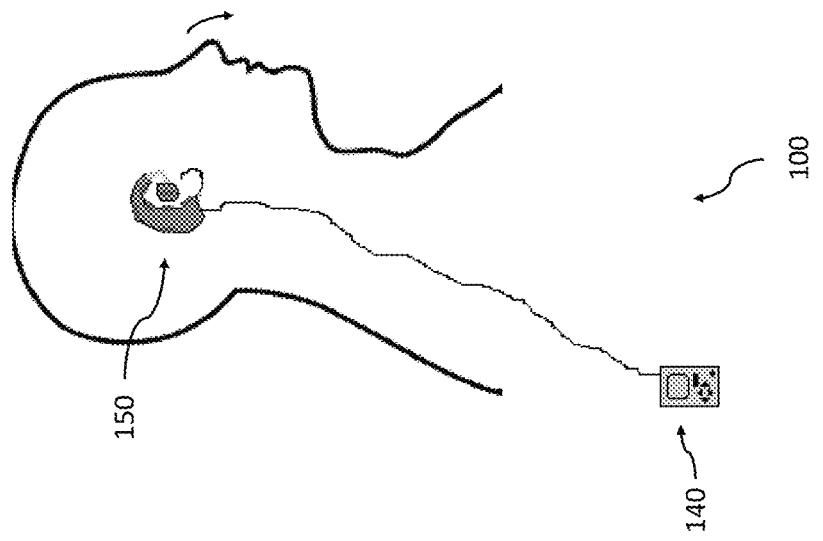
FIG. 3 illustrates a block diagram of an example apparatus in accordance with one or more embodiments.
Figure 4:
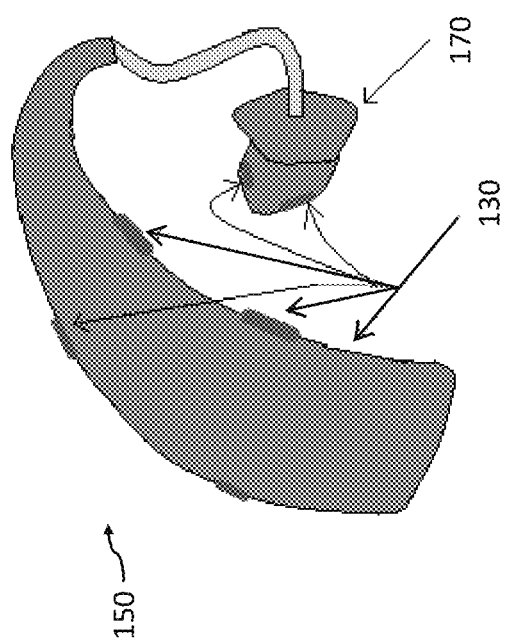
FIG. 4 illustrates a perspective view of an example apparatus in accordance with one or more embodiments.

The following detailed description includes references to the accompanying drawings, which form a part of the detailed description. The drawings show, by way of illustration, specific embodiments in which the apparatus may be practiced. These embodiments, which may also be referred to herein as "examples," "options," "configurations," or "implementations," are described in enough detail to enable those skilled in the art to practice the present embodiments. The embodiments may be combined, other embodiments may be utilized, or structural or logical changes may be made without departing from the scope of the invention. The following detailed description is, therefore, not to be taken in a limiting sense and the scope of the invention is defined by the appended claims and their legal equivalents.

Towards the need for improved systems and methods for assisting with both tinnitus and hearing loss (or compromised hearing such as in noisy environments), it is possible to affect neurons in the auditory brain to become more sensitive or less sensitive to sound features by combining sound stimulation with electrical stimulation of or near the ear region. For tinnitus, the ear region can be stimulated with electrical pulses that are precisely timed to customized sound features presented to the ear to be able to modify or suppress auditory neurons driving the tinnitus percept. For hearing aid enhancement, the ear region can be stimulated with electrical pulses that are timed to specific sound features that are arriving at the ear to be able to enhance or decrease auditory neuron's sensitivity to those features in the brain. In a sense, we are increasing or decreasing the brain's gain to those sound features rather than physically increasing or decreasing the volume of the sound that is arriving to the ear. Whether the brain's gain to those features is increased or decreased depends on whether the patient has deficits for those features such as due to hearing loss or being in a noisy environment, or has greater sensitivity to them that needs to be turned down. This novel approach can also reduce or avoid acoustic feedback issues for hearing aids since the physical sound delivered to the ear may not need to be dramatically increased to be effective.

Example systems and methods for treating tinnitus and/or hearing loss or enhancing hearing are described herein. In one or more configurations, an example apparatus includes a hearing aid device for hearing rehabilitation or enhancement that is combined and/or paired with electrical stimulation using coordinated (e.g., precisely timed) patterns relative to the sound input or output. The hearing aid device includes a sound input and a sound output. The apparatus further includes one or more electrodes communicatively coupled with the hearing aid device. The electrodes are configured to provide electrical stimulation to one or more of an area on a head near an ear or on or within the ear, where the electrical stimulation is synchronized with the sound input or output.

In one or more embodiments, the apparatus would present specific sound stimuli (e.g., pure tones, customized chords, bandwidth noise, phonemes, words, music or musical features) paired with electrical biphasic pulses (e.g., cathodic- or anodic-leading, different pulse widths and current levels, pulse bursts with certain pulse rates) presented in precisely timed patterns for several minutes (e.g., 10 minutes) to treat tinnitus. The patient would repeat this treatment as needed whenever the tinnitus returns or it is desired to further reduce the tinnitus.

In one or more embodiments, transcutaneous electrical nerve stimulation (TENS) of the head or ear region (i.e., activation of facial somatosensory nerves) is paired with acoustic stimulation into the ear. Through animal studies, we have demonstrated the ability to induce extensive plasticity in the auditory system when using this paired TENS-acoustic approach, which will be called "Multimodal Synchronization Therapy" (MST) in this disclosure. Neural plasticity induced by Multimodal Synchronization Therapy using the apparatus is significantly greater than TENS alone or acoustic stimulation alone. The changes in the auditory brain are those that are expected to alter the types of abnormal brain patterns occurring in tinnitus patients (i.e., hyperactivity or hypersynchrony). This Multimodal Synchronization Therapy approach could be delivered, for example, via a portable and wearable device similar to a hearing aid device to potentially treat millions of patients with subjective and bothersome tinnitus.

The stimulation of different sounds combined with electrical stimulation of the head/ear regions enhances plasticity (brain changes) in the auditory system relevant for tinnitus treatment. Our recent studies show that electrical stimulation of the ear region (pinna, mastoid region, and inner ear regions) with precise timing relative to the sound input causes greatly suppressed activity in the auditory system that is relevant for tinnitus treatment. Furthermore, using other delays can better enhance activity in the auditory system. This allows for hearing aids to perform better for hearing rehabilitation. By pairing electrical stimulation of the ear while the hearing aid is in use, hearing rehabilitation could be more greatly improved over time based on using the correct electrical pulses and the correct timing of the pulses relative to the sound input, particularly desirable sound features that are sent to the ear.

One or more example implementations involve transiently stimulating these different regions of the brain simultaneously, or with some interval, with electrodes associated with a hearing aid so that the inputs from the hearing aid and the electrodes reach these different brainstem and/or midbrain centers at the same time to cause a synchronized "shock" pattern that can then modify neurons, e.g., tinnitus-affected neurons. Activation of these different pathways can also activate other brain targets involved with plasticity and reinforcement that can modify neurons, e.g., tinnitus-affected neurons.

The number of areas stimulated by electrodes can, in certain embodiments, be up to 10, from 10-100, or from 100-1000, and in certain embodiments, more than 1000. This will effectively stimulate numerous sites across different surface regions in a temporally coordinated pattern. This provides coordinated timing of transient stimuli between multiple sites that are effectively synchronized with acoustic stimulation to provide the synchronized stimulation.

Referring to FIGS. 1-4, an apparatus 100 is shown. The apparatus includes a hearing aid device 150 with an audio generator 110 (which may include a sound input, such as a microphone, and a sound output, such as a loudspeaker), and one or more electrodes 130. The hearing aid device 150 may be coupled with an external controller and electrical stimulator 140 that can generate electrical pulses to be delivered using the one or more electrodes 130 (see FIGS. 1 and 3). A transceiver 160 may be included to allow sounds/sound signals to be wirelessly communicated with other devices. In other configurations, the electrical stimulator 140 and hearing aid device may be integrated into one component, such as by incorporating an electrical stimulator in the hearing aid device (see FIG. 2). In one or more implementations, the one or more electrodes 130 includes an array of electrodes. The one or more electrodes 130 may be strategically placed on the hearing aid housing where it touches near the ear, or touches the ear or mastoid (e.g., on the top of the ear, around the pinna, or even inside the ear canal when using an ear-insert type of hearing aid).

In one or more implementations, the hearing aid device 150 includes a wireless transceiver and power component (which may be integrated into the hearing aid device 150 or the controller/stimulator 140, and which may use, e.g., Bluetooth or other communications protocols) that powers the hearing aid and allows for, for example, communication of sounds and commands with other hearing aids or other devices. This wireless transceiver and power component could be worn on the body or around the neck to allow the hearing aids to be powered and controlled for sound and electrical stimulation.

In one or embodiments, an apparatus 100 for treating tinnitus and/or enhancing hearing includes hearing aid device 150 with electrodes 130 positioned in different locations along the hearing aid device that contacts the ear and/or an ear-insert 170 that goes into the ear canal with electrodes. Multiple electrodes 130 could be placed around or in the ear to steer current to the ear region. In one or more embodiments, the electrodes are integrated into the hearing aid device and have them contact the ear where the hearing aid already contacts ear, so there is no added complexity or additional pieces than what is already required for a hearing aid.

The apparatus includes a processor 180 that is configured to compute and process various stimulation strategies. The stimulation strategies are based on providing electrical pulses with varying amplitudes and shapes that are precisely timed relative to different parts of the sound input depending on whether the goal is to enhance hearing rehabilitation or suppress tinnitus/hyperacusis. For tinnitus, electrical pulses are presented with a set delay relative to a broadband noise or complex stimulus that is repeated multiple times to suppress the phantom percept. For hearing rehabilitation, the electrical pulses are synchronized to portions of the sound input that are low energy and difficult to hear. Conversely, the electrical pulses can be synchronized to portions of the sound input that are high energy and undesirable so as to suppress their perception or gain in the brain.

Training sessions can be used for both hearing improvement and tinnitus treatment. For example, certain types of sound stimuli and features that are usually difficult to hear for a given patient (e.g., high frequency information, specific speech elements, certain spectrotemporal patterns, etc.) are paired with ear electrical stimulation to enhance coding to those inputs. The user would simply plug in their hearing aid to a smartphone or online application that would guide them through the training session. This rehabilitation can also be done in real-time or in a natural environment as sound goes through the hearing aid and the processor determines portions that are low energy and synchronizes the electrical pulses to make the brain more sensitive to those features.

In one or more embodiments, a selection of different ear locations and delays of electrical pulses that suppress activity in the auditory system are paired with sound portions with higher energy to better balance the hearing across different energy ranges.

Initially this approach could be disruptive or confusing to hearing for some patients, but over time the brain would learn how to better detect the different features and improve hearing rehabilitation. In other words, the ear electrical stimulation serves as a strong driver of plasticity (i.e., brain changes) while the specific sound feature will shape what is changed in the brain.

Both of the primary functions being discussed (i.e., tinnitus treatment and hearing enhancement) could be achieved with the same hearing aid device since many patients with hearing loss also suffer from tinnitus. For example, patients could use one program during the day when they need hearing function and then a different program at night to treat their tinnitus. The tinnitus may be likely to return over time so treatments may need to be repeated daily, every few days, weekly, etc. Since hyperacusis is also linked to hyperactivity in the auditory system, this approach may also treat hyperacusis. Across tinnitus, hyperacusis, and hearing rehabilitation, more than 5% of the population could benefit from such hearing aid devices. Better hearing rehabilitation is possible than with current hearing aids by enhancing brain changes to adapt to the lower amount and altered type of sound information that gets delivered to patients with hearing loss using typical hearing aids. The device is also for treating tinnitus or hyperacusis.

Figure 5:
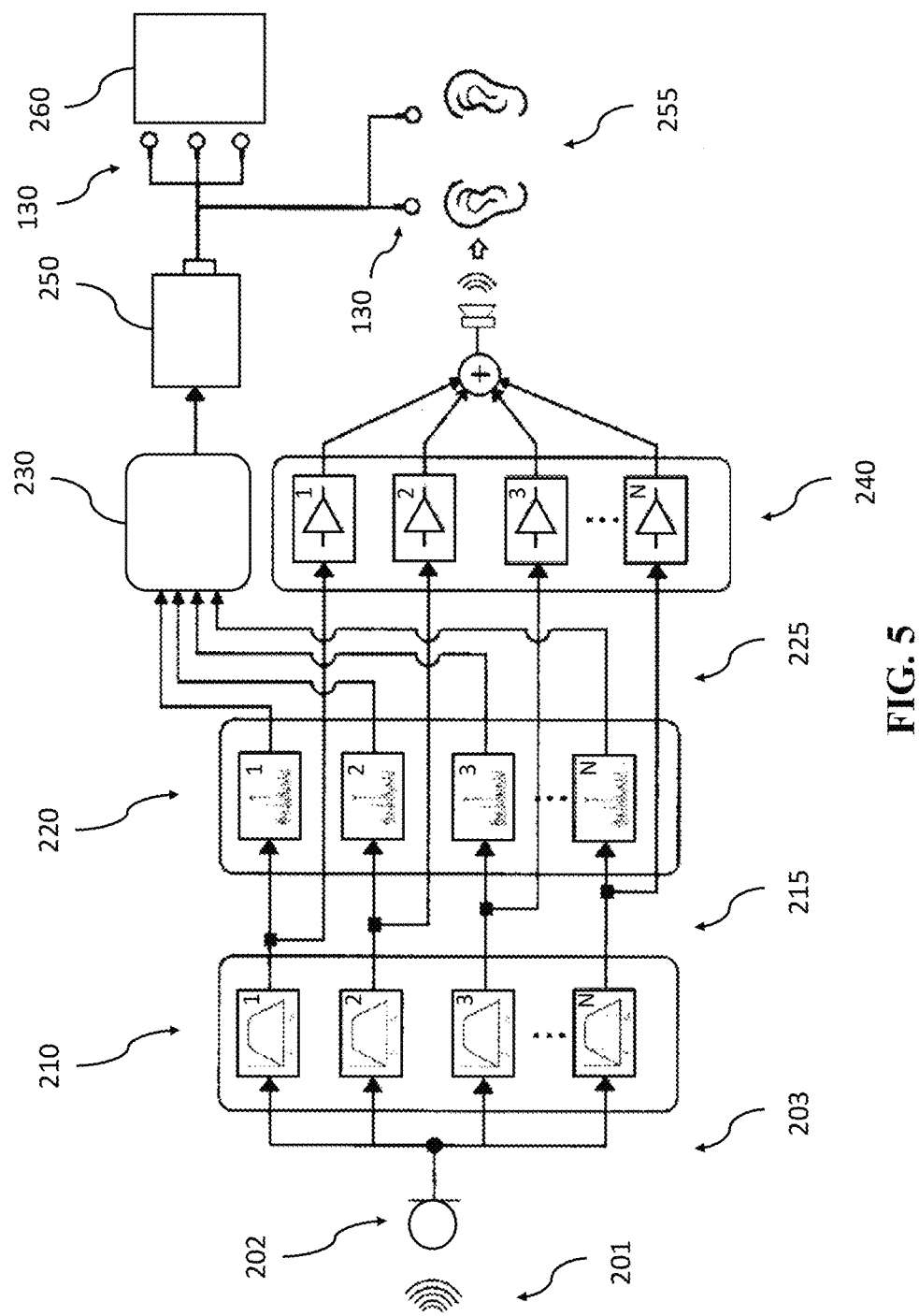
FIG. 5 illustrates a schematic view of an example apparatus in accordance with one or more embodiments.

FIG. 5 illustrates a block diagram of the implementation of a hearing aid device for hearing enhancement. Surrounding sound 201 is picked up by sound input 202 (e.g., a microphone), and transduced to a time-domain electrical signal 203. In one or more embodiments, a preamplifier can also be used to increase the signal-to-noise ratio, based on the sensitivity and internal noise of the microphone. In example implementations, the processor 180 of the hearing aid device 150 is configured to analyze and modify the signal as follows.

The time domain signal 203 from the microphone 202 (or optional preamplifier) passes through multiple band-pass filters 210 of difference ranges, for example within 50 Hz to 12 KHz to split the signal into multiple frequency bands 215. The output of each band-pass filter 210 is fed to its respective feature detector 220 that detects peak or other feature over time when the energy is high in the given frequency band. The band-limited signal 230 from each band-pass filter 210 is amplified by the respective amplifier 240 based on the prescribed gain that is derived from the audiogram.

The detector 230 finds a high peak energy in each frequency band where there is deficit in the audiogram and electrically stimulates the patient using the electrical stimulator 250 to stimulate the electrodes 130 with electrical pulses. The stimulus is synchronized with the sound input and occurs at a time with an optimized delay for the device to enhance the deficits in the audiogram. There may be situations where electrical stimulation in a frequency band can have minimal deficit to suppress those components relative to deficit channels with appropriate delay. The detector 230 triggers the electrical stimulator to stimulate one or both ears 255, head or other body locations 260 with one or more electrodes 130, or an array of electrodes 130.

The electrical pulses include one of more of the following: biphasic or monophasic pulses or even biphasic pulses with a gap between the phases of the pulse (known as interphase gap); negative leading or positive leading phase first; pulse widths: 10 microseconds to 1000 microseconds; interphase gap: 0 ms to 500 microseconds. The intensity of the current can be increased until body sensation is obtained. In one or more embodiments, the pulses can be presented at a subthreshold level, suprathreshold but comfortable level, or a slightly uncomfortable level which will be fitted to each patient.

In one or more embodiments, the electrical pulse patterns include a single pulse synchronized to each feature of the sound signal. The electrical pulse patters optionally include bursts of pulses synchronized to each feature of the sound signal that consists of 2-20 pulses with a pulse rate of 100-5000 Hz. In one or more embodiments, the pulses can be amplitude modulated or variations in intensity for each pulse of the burst of pulses, i.e., the pulses do not need to be the same intensity.

In one or more embodiments, there is a delay 120 between electrical pulses and sound feature, which is synchronized. In one or more embodiments, the delay is about −20 ms up to about +20 ms. In other embodiments, the delay is about −100 ms up to about +100 ms.

Synchronized stimulation refers to transient stimulation (e.g., 0.01-100 ms) of at least two different pathways in a specific time relative to each other (e.g., 0-100 ms). The timing is designed and optimized to induce effective activation of one or more specific brain regions to affect the tinnitus percept while other brain regions are not effectively activated because the timing is not optimized for those regions. The timing can also be designed to affect hearing rehabilitation. In turn, this allows for targeted brain activation without having to actually implant and stimulate invasively within those regions. Effectively refers to the ability to alter the tinnitus percept to a subjectively improved state (e.g., not only suppression but also any alteration that could still improve the subjective tinnitus state).

An innovation described herein is a low-cost treatment that achieves both noninvasiveness and specificity. It takes advantage of the dense and coordinated interconnectivity across sensory, motor, cognitive, and limbic centers. One center may exhibit abnormal activity driving the neurological disorder. A goal of the treatment is to activate specific pathways related to the other modalities and with appropriate timing to then modulate and "fix" or compensate for the abnormal region. This assumes that these different pathways can interact and induce plasticity across centers, which is expected considering the necessity for precise coordination and reinforcement among these modalities during daily function and survival.

Each neuron of the brain receives inputs from many different neurons and can be affected by multiple sensory, motor, cognitive, and limbic modalities. Therefore, there is more than one means to affect a given neuron, and thus activating as many of those ways as possible and in a synchronized pattern would elicit artificial and strong activation of that neuron to alter its state. Repetitive activation of that neuron or groups of neurons would then lead to long-term plasticity, shifting it away from the abnormal state and suppressing the neurological condition (e.g., tinnitus). The treatment may need to be applied periodically since it may not cure the neurological condition but rather eliminate the debilitating symptoms.

One embodiment of this approach is for tinnitus suppression that applies coordinated activation of auditory and somatosensory pathways. A topographic organization of neurons within the auditory midbrain was discovered that can be differentially activated by different body locations in guinea pig. In other words, stimulation of different combinations of body locations (e.g., ear regions but also can include face, head, tongue, neck, body, and limb regions) with appropriate delays appears to activate different and specific neurons across the auditory midbrain, which in turn projects to other regions throughout the auditory system through ascending and descending pathways. Thus a treatment described herein enables localized auditory activation without having to actually implant an electrode into the brain. Customized acoustic stimuli can then be used to reinforce or interact with those activated midbrain neurons that in turn would modulate and potentially induce plasticity across the auditory system. Other embodiments of this treatment would incorporate other reinforcement inputs, such as visual cues, cognitive/emotional effects, reward/pleasurable stimuli, and slightly painful stimuli that could all contribute to synchronization and enhanced plasticity within the brain. This multimodal synchronization therapy is not limited to treating tinnitus. For example, it could be used to treat pain or hearing loss as discussed above.

The described treatment and apparatus can provide a powerful way to noninvasively modulate tinnitus-affected neurons and/or treat hearing loss. It can also be implemented with low cost hardware and surface electrodes that can be easily miniaturized for portability and take-home usage, expanding on transcutaneous electrical nerve stimulation (TENS) devices safely used for pain or massage therapy. In order to investigate the numerous stimulation parameters directly in humans and identify the optimal settings, it is possible to pursue what is termed a heuristic translational approach. A low cost device can be implemented that could be distributed across a large patient group and taken home for continuous optimization by the patients. A simple example would be to have a digital device with a knob that can scroll through the different stimuli that are preset during the clinical fitting session. The patient would input a rating into their device for each setting that effectively reduces their tinnitus or improves their hearing. The device would continue to adjust the stimulation parameters based on these ratings to converge towards an optimal setting. Self-fitting through a heuristic translational approach is one way the treatment can be fitted across a large number of patients and stimulation parameters. The patients are able to invest a considerable amount of time optimizing their own device. Any signs of improvement in their tinnitus and/or their hearing with this treatment will provide significant motivation for the patients to continue optimizing their own device. Another advantage of a heuristic translational approach is that it is not necessary to understand the neural mechanisms of each type of tinnitus to improve the treatment. Instead, the device may be heuristically optimized for each patient, which can overcome the issue of patient variability. The patients could also connect to an online server and database in which they can download new software for their device as well as upload their device parameters and progress. This online interaction with the patients would allow collection of an enormous amount of data across a large population to identify appropriate stimulation patterns for different types of tinnitus patients. The patients can also interact with other patients and skilled personnel to help each other as well as improve the tinnitus treatment.

An innovation of MST using the apparatus is that it can achieve both specificity and noninvasiveness, and can be optimized using a heuristic translational approach. MST takes advantage of the dense and coordinated interconnectivity across sensory, motor, cognitive, and limbic centers. One center may exhibit abnormal activity driving the neurological disorder. A goal of MST is to activate specific pathways related to the other modalities to then modulate and fix the abnormal region. This assumes that these different pathways can interact and induce plasticity across centers, which seems likely considering the necessity of precise coordination and reinforcement among these modalities during daily function and survival. MST can be used for tinnitus suppression or hearing enhancement/improvement through coordinated activation of auditory and somatosensory pathways.

Integrative role of inferior colliculus relevant for the treatment: The inferior colliculus (IC) is the principle midbrain nucleus of the auditory pathway and receives input from several more peripheral brainstem nuclei in the auditory pathway, as well as inputs from the auditory cortex. The inferior colliculus has three subdivisions: the central nucleus (ICC), a dorsal cortex by which it is surrounded, and an external cortex, which is located laterally. Its multimodal neurons are implied in auditory-somatosensory interaction, receiving projections from somatosensory nuclei. The input connections to the inferior colliculus are composed of many brainstem nuclei. All nuclei except the contralateral ventral nucleus of the lateral lemniscus send projections to the central nucleus bilaterally. It has been shown that a great majority of auditory fibers ascending in the lateral lemniscus terminate in the central nucleus. In addition, the IC receives inputs from the auditory cortex, the medial division of the medial geniculate body, the posterior limitans, suprapeduncular nucleus and subparafascicular intralaminar nuclei of the thalamus, the substantia nigra, pars compacta lateralis, the dorsolateral periaqueductal gray, the nucleus of the brachium of the inferior colliculus, deep layers of the superior colliculus, reticular activating nuclei, limbic nuclei, and other modulatory centers. The inferior colliculus receives input from both the ipsilateral and contralateral cochlear nucleus and respectively the corresponding ears. The medial geniculate body is the output connection from inferior colliculus and the last subcortical way station. The medial geniculate body is composed of ventral, dorsal, and medial divisions, which are relatively similar in humans and other mammals. The ventral division receives auditory signals from the central nucleus of the IC.

As stated above, stimulation of different sounds combined with electrical stimulation of different regions could enhance plasticity (brain changes) in the auditory system. We have discovered that electrical stimulation of the ear region, including pinna, mastoid region, and inner ear regions, with precise timing relative to the sound input causes greatly suppressed or enhanced activity.

Figure 6:
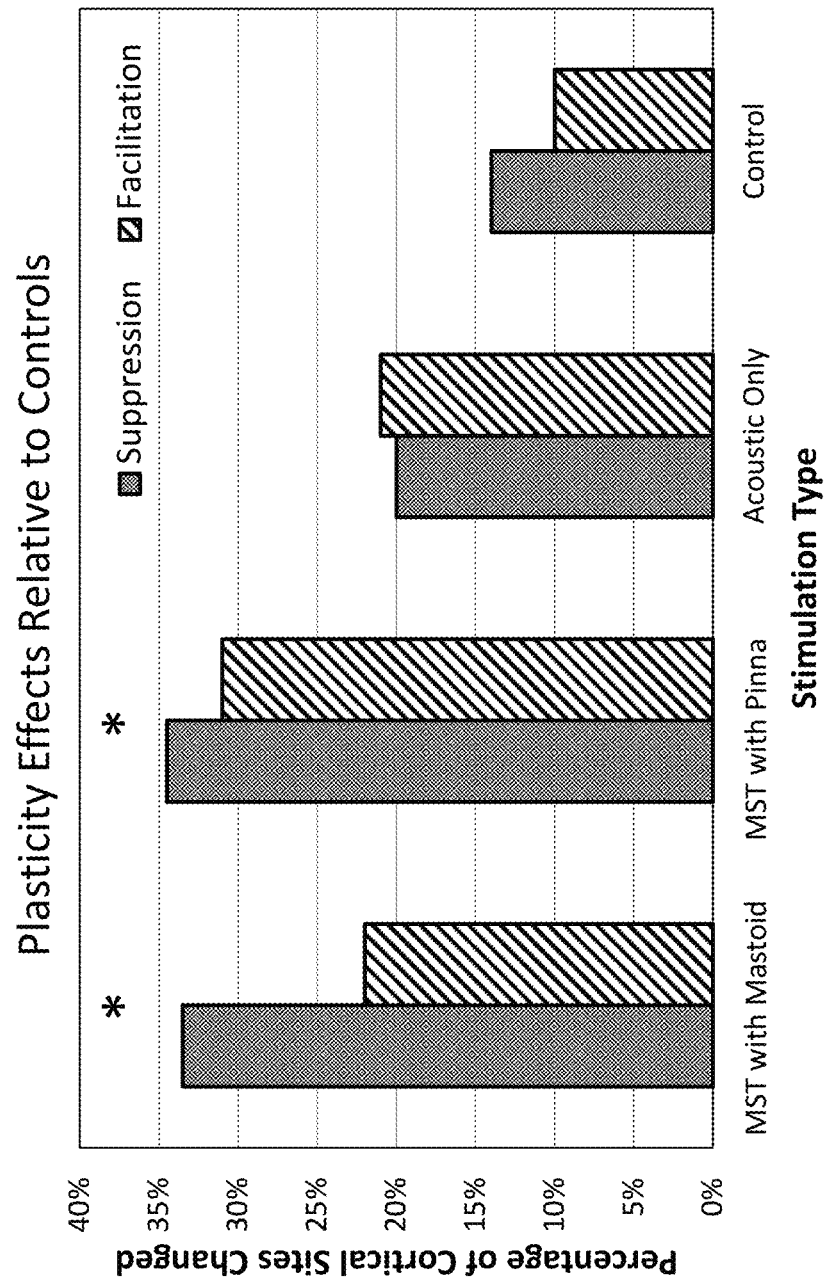
FIG. 6 illustrates a study in which broadband noise acoustic stimulation was paired with electrical stimulation of either the mastoid area or the pinna for stimulation using the apparatus in accordance with one or more embodiments, and demonstrates the ability to greatly enhance or suppress the auditory brain compared to non-paired stimulation.

FIG. 6 illustrates a study in which broadband noise acoustic stimulation was paired with electrical stimulation of either the mastoid area or the pinna for stimulation using the apparatus. Acoustic-driven activity before and 30 minutes after was compared to determine if acoustic-driven firing had been altered, and the percent of sites suppressed (left bars) and facilitated (right bars) are shown here. For the acoustic only condition, broadband noise stimulation alone was used. For the control condition, no stimulation was used. The apparatus 100 consistently caused more changes than acoustic alone and control regardless of body stimulation location (* $p<0.05$). The apparatus 100 with mastoid stimulation was always more suppressive than facilitative regardless of inter-stimulus delay, while the apparatus with pinna stimulation was inter-stimulus delay-dependent as seen in FIG. 7.

Figure 7:
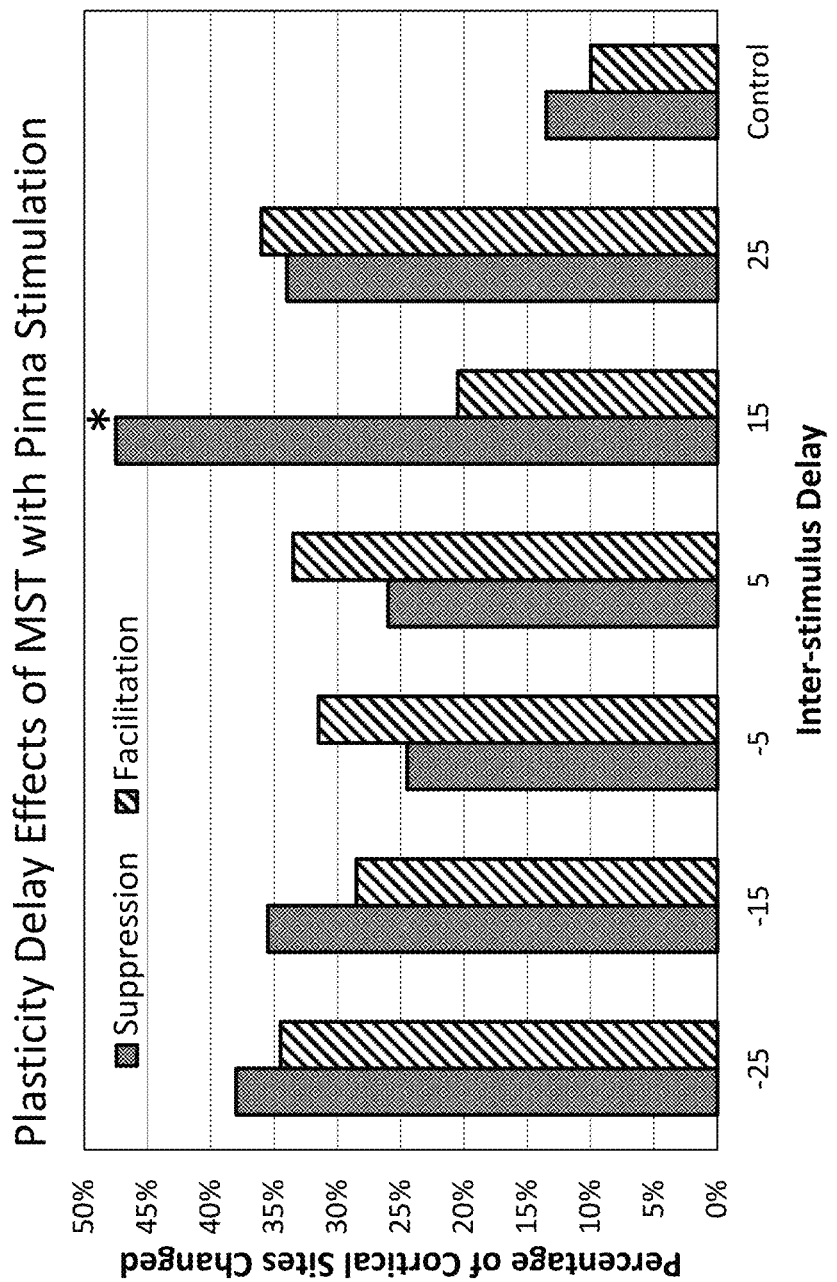
FIG. 7 illustrates a study in which broadband noise acoustic stimulation was paired with electrical stimulation of pinna at different inter-stimulus delays (e.g. −25 indicates pinna stimulation preceding acoustic stimulation by 25 ms) for stimulation using the apparatus in accordance with one or more embodiments, and demonstrates the critical importance in the timing of the paired stimuli to either enhance or suppress the auditory brain. The effective delay ranges exist within a −100 to +100 ms range.

In the study depicted in FIG. 7, broadband noise acoustic stimulation was paired with electrical stimulation of pinna at different inter-stimulus delays (e.g. −25 indicates pinna stimulation preceded acoustic stimulation by 25 ms) for stimulation using the apparatus 100.

Acoustic-driven activity before and 30 minutes after was compared to determine if acoustic-driven firing had been altered, and the percent of sites suppressed (left bars) and facilitated (right bars) are shown here. For the control condition, the apparatus 100 was replaced with no stimulation. The apparatus 100 consistently caused more changes than control regardless of inter-stimulus delay location ($p<0.05$). One inter-stimulus delay (15 ms) caused more suppression than facilitation (* $p<0.05$), while other delays did not, indicating that inter-stimulus delay plays a significant role in plasticity effects.

We discovered that pinna (and many other somatosensory pathways) project heavily and excite the auditory system, such as in the inferior colliculus (IC). This gives further evidence that somatosensory (including mastoid and pinna) stimulation can be combined with acoustic stimulation to cause converging effects onto different neurons in the auditory system, such as in the inferior colliculus or auditory cortex.

Figure 8:
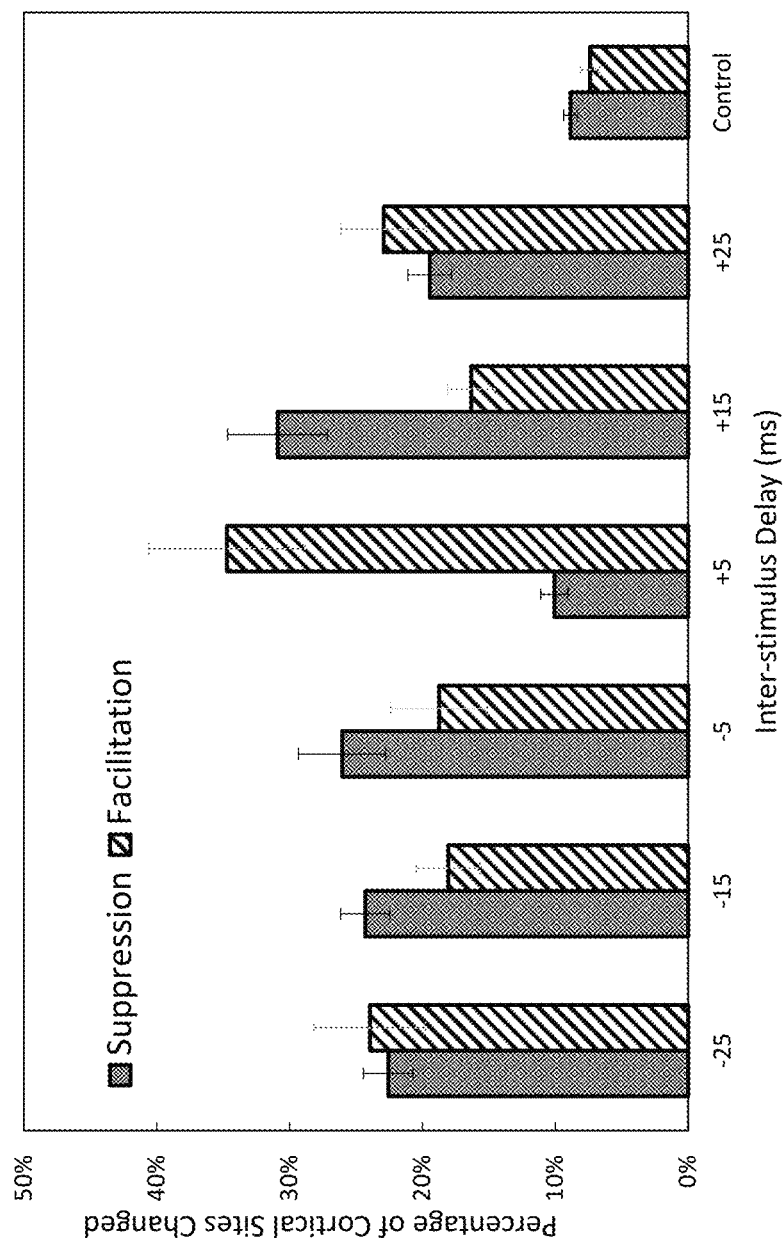
FIG. 8 illustrates a study similar to the study in FIG. 7, except the animals were awake and relaxed (i.e., not anesthetized), and further demonstrates the critical importance in the timing of the paired stimuli to either enhance or suppress the auditory brain, as well as in controlling a subject's stress or relaxation state. The effective delay ranges exist within a −100 to +100 ms range.

Referring to FIG. 8, a similar study as in FIG. 7 was performed except that the animals were not anesthetized. Instead the animals were awake and relaxed through stress-relieving and handling techniques. The apparatus 100 not only demonstrated the ability to cause more systematic suppressive effects that was inter-stimulus delay dependent, but also the ability to cause more systemic enhancement effects over the control cases. In other words, these data demonstrate that in awake and relaxed states (more similar to what would happen in human subjects in the comfort of their homes or daily environments) apparatus can be used with precisely-timed delays between acoustic stimulation and somatosensory electrical stimulation to shape and modify auditory brain patterns that could suppress or enhance sensitivity to different sound features.

Figure 9:
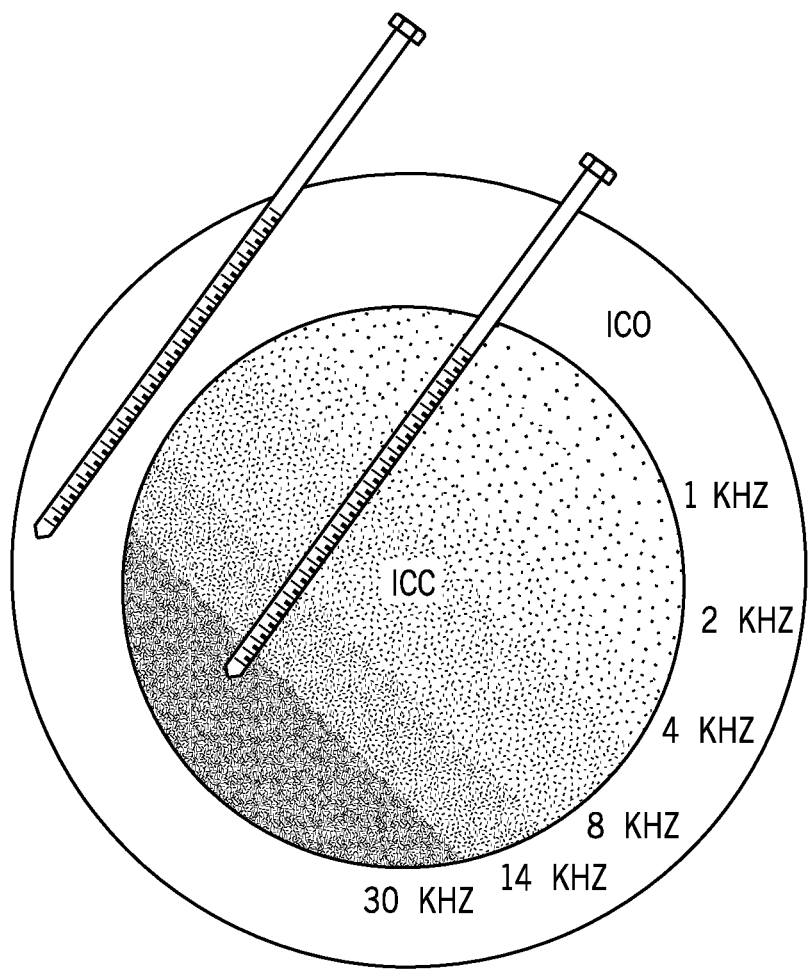
FIG. 9 illustrates an example of a typical recording electrode placement in the inferior colliculus (IC), where one electrode shank with multiple sites is in the central nucleus of the inferior colliculus (ICC; has different regions sensitive to different frequencies in an orderly pattern) and one electrode shank with multiple sites is in the external region of the inferior colliculus (ICO).
Figure 10:
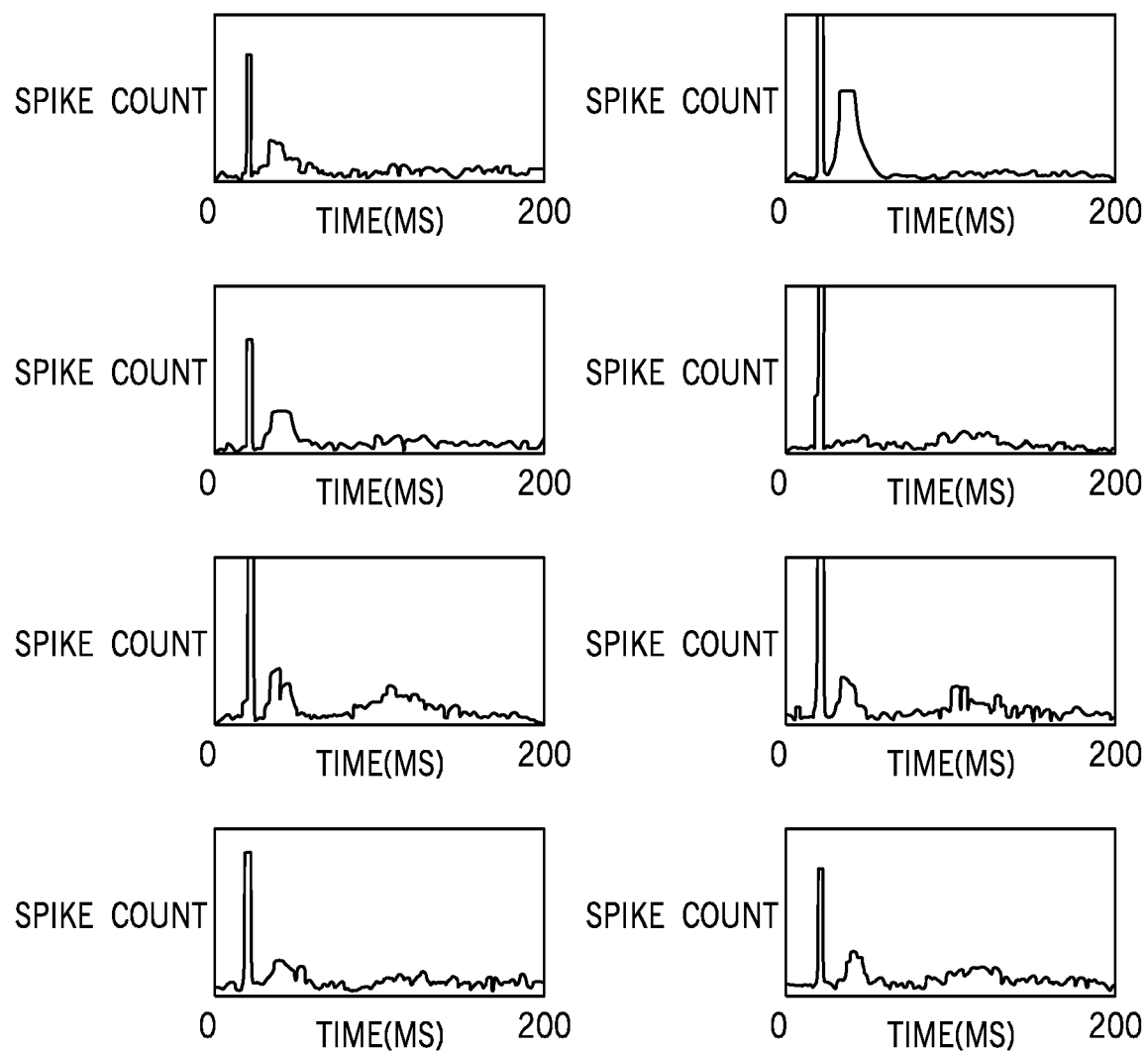
FIG. 10 illustrates examples of post-stimulus time histograms (PSTHs) of IC neural activity in response to electrical pinna stimulation, where the PSTHs are histograms of when neural spikes occur across 100 trials of stimulation in response to electrical stimulation of the pinna in accordance with one or more embodiments.

Referring to FIG. 9, this shows an example of a typical recording electrode placement in the IC, where one electrode shank is in the central nucleus of the inferior colliculus (ICC) and one electrode shank is in the external region of the inferior colliculus (ICO). The graphs of FIG. 10 are examples of post-stimulus time histograms (PSTHs) of IC neural activity in response to electrical pinna stimulation. Note that the PSTHs are histograms of when neural spikes occur across 100 trials of stimulation in response to electrical stimulation of the pinna. In all eight PSTHs, an electric artifact from pinna stimulation can be found at 20 ms. Following this artifact, one can see neural responses at various latencies. In some cases, two peaks exist in the same PSTH, indicating that we may be activating more than one pathway or more than one type of axon fiber.

For tinnitus treatment, timing between ear/somatosensory electrical stimulation and sound stimulation may be critical for causing suppressive or enhancive changes in neural activity in the auditory system. Considering that tinnitus has been linked to hyperactivity and hypersynchrony in the auditory brain, and we can achieve significant suppression of auditory activity using this multimodal stimulation with specific delays, the apparatus described herein can suppress tinnitus by identifying the appropriate timing parameters of stimulation in humans. Furthermore, since the brain is quite variable across individuals, the fitting process allowed with the apparatus is advantageous. The patient may be allowed to select different electrodes located in different parts of the ear/head in contact with the hearing aid device and different timing patterns until the patient observes a decrease in his or her tinnitus. Multiple settings may be stored in the device and the patient will apply stimulation for a period of time (e.g., about 10 minutes) per day, or as needed to decrease the tinnitus. The apparatus can thus be used to suppress tinnitus when needed. Most hearing aid companies have pushed forward their own acoustic stimulators to attempt to mask or decrease tinnitus with sound stimulation alone. This novel invention provides a stronger method of combined sound stimulation with precisely-timed and synchronized electrical pulse patterns to the ear or near the ear region.

In addition, the apparatus can provide an integrated hearing aid that is portable and easily worn whenever the tinnitus needs to be suppressed. Neuromodulation effects do not cure tinnitus but temporarily suppress the tinnitus percept, which usually can last for hours and up to several weeks. The patient may need to receive the treatment using the apparatus on a daily or weekly basis for about tens of minutes (or different durations for different patients).

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

The invention claimed is:

1. A method for treating one or more of tinnitus or hearing loss, the method comprising:
   collecting incoming sound using one or more of a microphone, a recording device, a mobile phone, and/or a sound generator, and transducing the incoming sound to a sound signal;
   passing the sound signal through one or more band pass filters;
   detecting a feature or features of the sound signal over time;
   modifying the sound signal based on feature detection;
   delivering the modified sound signal through a sound output; and
   using surface electrodes to deliver an electrical stimulus to a surface of an ear via electrical pulses, where the electrical stimulus directly modulates a tinnitus-affected neuron, and where delivery of the electrical stimulus is coordinated with delivery of the modified sound signal through the sound output with a delay greater than 0.01 ms and less than or equal to 100 ms, and where delivery includes using the detected feature or features to enhance or suppress brain sensitivity to the feature or features.

2. The method as recited in claim 1, further comprising amplifying the sound signal prior to delivering the signal through the sound output.

3. The method as recited in claim 1, further comprising determining a delay to enhance deficits in the incoming sound, and delaying delivery of the sound signal based on the determined delay.

4. The method as recited in claim 1, wherein delivering electrical stimulus includes delivering electrical stimulus to one or more areas of the ear selected from the group of regions consisting of a mastoid region, a pinna region, and an inner ear region.

5. The method as recited in claim 1, further comprising delivering specific sound stimuli through the sound output while delivering electrical pulses with the electrodes to suppress unwanted sounds or to enhance hearing to desired sounds.

6. The method as recited in claim 5, wherein presenting specific sound stimuli includes presenting one or more of pure tones, customized chords, or bandwidth noise.

7. The method of claim 5, wherein presenting sound stimuli includes presenting specific words, phonemes, features of words, music, or features of music.

8. The method of claim 5, wherein presenting sound stimuli includes presenting speech or speech features in noise to enhance sensitivity to the speech or speech features, and reduce sensitivity to the noise or unwanted sounds.

9. The method as recited in claim 1, further comprising pairing the presented specific sound stimuli with electrical biphasic or monophasic pulses in timed patterns.

10. The method of claim 9 wherein the electrical pulses have a constant pulse rate of repeated pulses, or are varying inter-pulse timed pulses based on when sound features are detected, to enhance or suppress sensitivity to certain sound features that occur over time via single electrical pulses or bursts of electrical pulses.

11. The method of claim 10, wherein the electrical pulses or bursts of pulses are constant amplitude or amplitude modulated over time, wherein the bursts of pulses have pulse trains with a range of 100 pps to 5000 pps.

12. The method as recited in claim 9, where delivery of the electrical stimulus is synchronized with detected features of the signal with each pulse or burst of pulses.

\* \* \* \* \*